United States Patent
Ng et al.

(10) Patent No.: US 10,286,398 B2
(45) Date of Patent: May 14, 2019

(54) APPARATUS AND METHOD FOR SEGMENTED THERMAL CYCLER

(71) Applicant: LIFE TECHNOLOGIES CORPORATION, Carlsbad, CA (US)

(72) Inventors: Hwee Tian Ng, Singapore (SG); Huei Yeo, Singapore (SG); Wei Hsien Choo, Singapore (SG)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 14/617,831

(22) Filed: Feb. 9, 2015

(65) Prior Publication Data

US 2015/0217292 A1    Aug. 6, 2015

Related U.S. Application Data

(63) Continuation of application No. 12/617,568, filed on Nov. 12, 2009, now abandoned.

(Continued)

(51) Int. Cl.
*B01L 7/00* (2006.01)
*B01L 9/00* (2006.01)
*C12Q 1/686* (2018.01)

(52) U.S. Cl.
CPC ............... *B01L 7/52* (2013.01); *C12Q 1/686* (2013.01); *B01L 9/523* (2013.01);
(Continued)

(58) Field of Classification Search
CPC .... B01L 7/52; B01L 9/523; B01L 2200/0689; B01L 2300/0654; B01L 2300/0829; B01L 2300/041; B01L 2300/0663; B01L 2300/1833; B01L 2300/1894; B01L 2300/1822; C12Q 1/686

See application file for complete search history.

(56) References Cited

U.S. PATENT DOCUMENTS

| 8,198,051 B2 | 6/2012 | Schicke et al. |
| 2004/0018610 A1* | 1/2004 | Sandell ............ G01N 21/0332 435/287.2 |

(Continued)

FOREIGN PATENT DOCUMENTS

WO    2008/030914    3/2008

OTHER PUBLICATIONS 200907554-0, Hungarian IP Office Search Report and Written Opinion.

*Primary Examiner* — Gautam Prakash
(74) *Attorney, Agent, or Firm* — François A. Pelaez

(57) ABSTRACT

The present invention relates to a thermal cycler for the carrying out of chemical or biological reactions, such as PCR or other nucleic acid amplification reactions, that is segmented with a plurality of reaction vessel receiving elements. The reaction vessel receiving elements are thermally isolated from each other and provide an airtight seal to prevent liquids or moisture from penetrating below the reaction vessel receiving elements. The reaction vessel receiving elements have several recesses arranged in a pattern to receive the reaction vessels of a single standard microtiter plate and the segmented thermal cycler has a system for independently heating and cooling each of the reaction vessel receiving elements.

18 Claims, 10 Drawing Sheets

Related U.S. Application Data

(60) Provisional application No. 61/114,902, filed on Nov. 14, 2008.

(52) U.S. Cl.
CPC . *B01L 2200/0689* (2013.01); *B01L 2300/041* (2013.01); *B01L 2300/0654* (2013.01); *B01L 2300/0663* (2013.01); *B01L 2300/0829* (2013.01); *B01L 2300/1822* (2013.01); *B01L 2300/1833* (2013.01); *B01L 2300/1894* (2013.01)

(56) References Cited

U.S. PATENT DOCUMENTS

| | | |
|---|---|---|
| 2006/0141612 A1 | 6/2006 | Yamamoto et al. |
| 2007/0077657 A1 | 4/2007 | Carlson et al. |
| 2007/0184548 A1 | 8/2007 | Tan et al. |
| 2008/0274511 A1* | 11/2008 | Tan et al. ............ B01L 3/50855 435/91.2 |

* cited by examiner

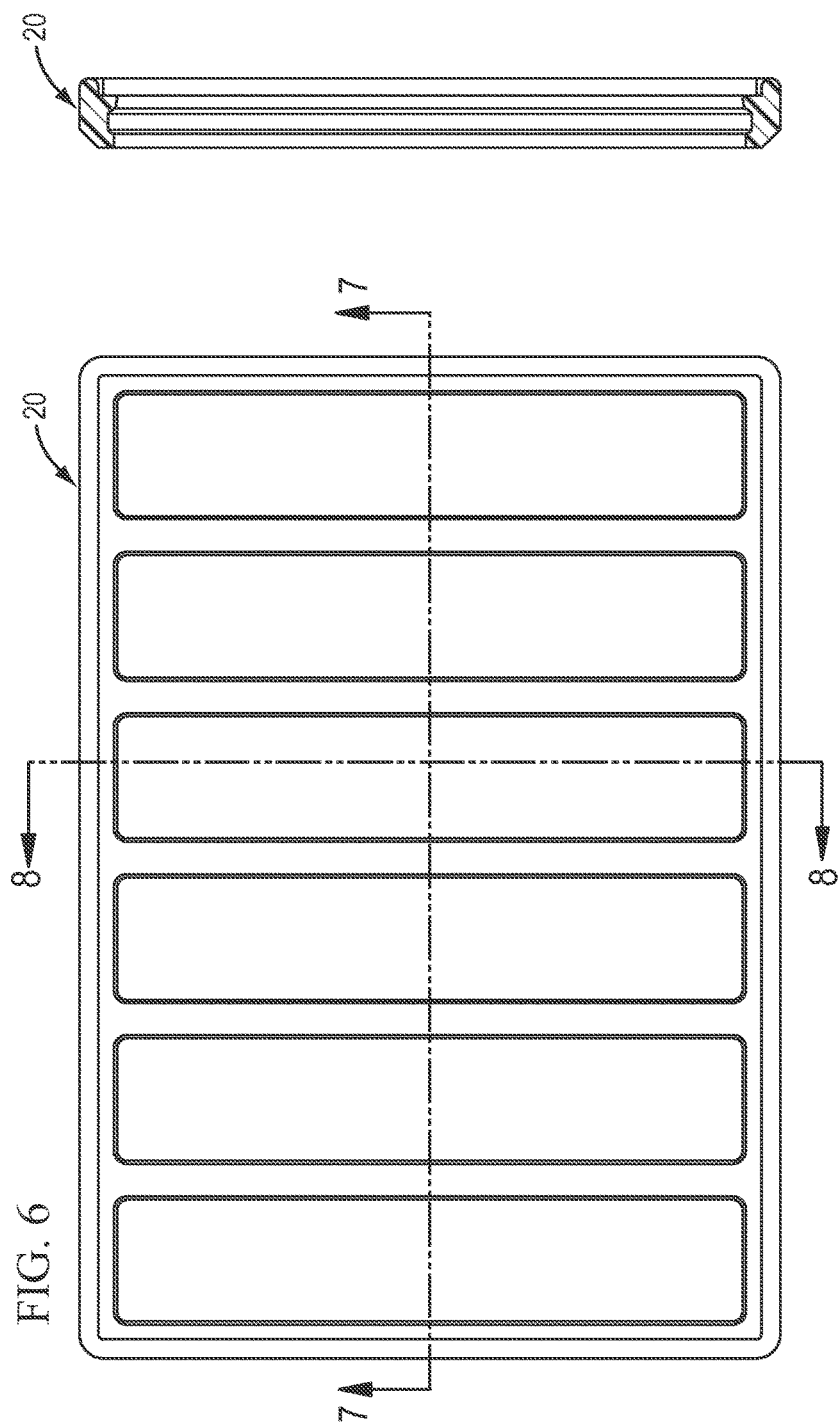

APPARATUS AND METHOD FOR SEGMENTED THERMAL CYCLER

CROSS-REFERENCE TO RELATED APPLICATION

This application is a continuation of U.S. application Ser. No. 12/617,568 filed Nov. 12, 2009, which claims a priority under 35 U.S.C. § 119(e) from U.S. Provisional Application No. 61/114,902 filed Nov. 14, 2008, all of which are incorporated herein by reference.

FIELD OF THE INVENTION

The present invention relates to a thermal cycler for the carrying out of chemical or biological reactions, such as PCR or other nucleic acid amplification reactions, the thermal cycler is segmented in that it has a plurality of reaction vessel receiving elements separated and thermally isolated from each other for receiving reaction vessels, wherein the reaction vessel receiving elements have several recesses arranged in a pattern to receive the reaction vessels of a single standard microtiter plate. The segmented thermal cycler has a system for independently heating and cooling each of the reaction vessel receiving elements.

INTRODUCTION

Testing of biological or chemical samples often requires a device for repeatedly subjecting multiple samples though a series of temperature cycles. Such devices are described as thermal cyclers or thermocycling devices and are used to generate specific temperature cycles, i.e. to set predetermined temperatures in the reaction vessels and to maintain predetermined intervals of time, sometimes called protocols. Often times it is desirable to thermocycle different samples in a single vessel array through different protocols by varying temperature, time, and/or number of cycles, where these experiments can be carried out simultaneously.

For example, such tests can used to determine the optimal denaturing temperature, the optimal annealing temperature, and the optimal elongation temperature of a PCR reaction. To achieve this, the same reaction mixture is poured into the individual reaction vessels, and the temperature cycles necessary to perform the PCR reaction are executed. Such a temperature cycle comprises the heating of the reaction mixture to the denaturing temperature, which usually lies in the range 90°-95° C., cooling to the annealing temperature, which is usually in the range 40°-60° C. and heating to the elongation temperature, which is usually in the range 70°-75° C. If desired, the time of each cycle can also be varied. A cycle of this kind is repeated several times, leading to amplification of a predetermined DNA sequence. The annealing temperature, at which the primer is added, has a powerful influence on the result. However the elongation temperature too can have beneficial or adverse effects on the result. At a higher elongation temperature, the addition of the bases is accelerated, with the probability of errors increasing with higher temperature. In addition, the life of the polymerase is shorter at a higher elongation temperature. Another important parameter for the success of a PCR reaction is the different residence volumes spread over different reaction vessels. Problems arise with conventional devices as these parameters can not be varied in one test series for an individual reaction vessel holder. To test different residence volumes, several test series are required and are performed either consecutively in one thermocycling device or simultaneously in several thermocycling devices.

Historically, only temperature could be varied during thermal cycling using a gradient thermal cycler that can create a temperature gradient and/or a gradient block as described in, for example, U.S. Pat. Nos. 5,525,300 and 7,074,367. The disclosed devices have a single block and create a gradient of temperatures and then try to designate different temperature for samples.

The next generation of thermal cyclers adopted a markedly different approach. Rather than a single gradient block, these new thermal cyclers embodied a plurality of blocks or reaction vessel receiving elements that are isothermal where each reaction vessel receiving element is independently controlled and can be programmed with different protocols, while having the proximity to be arranged in a pattern to receive the reaction vessels of a single vessel array of a standard format as described in, for example, U.S. Pub. No. 2006-0228268. Different but predetermined temperatures are set for each of the reaction vessel receiving elements. After completion of the cycles it is possible to determine, with the aid of the reaction products, those temperatures at which the PCR reaction will give the user the optimal result. Here the result may be optimized e.g. in respect of product volume or also product quality. The present invention is an improvement to such a thermal cycler, by providing a different means for thermal isolation of the reaction vessel receiving elements and a seal to reduce the ability of liquids and moisture from penetrating between the reaction vessel receiving elements.

SUMMARY OF THE INVENTION

According to various embodiments, the present teachings describe a thermal cycler for processing biological or chemical samples with a plurality of reaction vessel receiving elements configured to receive one standard microtiter plate, a plurality of thermoelectric cooling devices (TEC) disposed to correspond to each of the plurality of reaction vessel receiving elements, wherein the TEC provides heating and cooling, a drip pan positioned above the TECs and framing the plurality of reaction vessel receiving elements, a single gasket to seal the plurality of reaction vessel receiving elements, wherein the gasket has a convex construction, and a clamp to provide lateral force to compress the gasket between the reaction vessel receiving elements, wherein the gasket forms an airtight seal between each of the plurality of reaction vessel receiving elements and between the drip pan and the plurality of reaction vessel receiving elements to isolate the plurality of TECs from environmental conditions above the drip pan and the plurality of reaction vessel receiving elements, and wherein the gasket is composed of non-thermally conducting material and separates adjacent reaction vessel receiving elements to provide thermal isolation between adjacent reaction vessel receiving elements.

According to various embodiments, the present teachings describe a method for processing biological or chemical samples including positioning a single standard microtiter plate on a plurality of reaction vessel receiving elements of a thermal cycler, independently heating and cooling the plurality of reaction vessel receiving elements with a plurality of thermoelectric cooling devices (TEC), sealing the area below the plurality of reaction vessel receiving elements with a drip pan, a gasket, and a clamp, wherein the gasket has a convex portion and the clamp provides a lateral force to compress the gasket between the reaction vessel receiving elements to form an airtight seal between each of the plurality of reaction vessel receiving elements, and thermally isolating adjacent reaction vessel receiving elements by constructing the gasket from a non-thermally conducting material.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIGS. 5 and 6 depict a perspective view and a side view of a gasket, according to various embodiments;

FIGS. 7 and 8 depict cross-sectional views of the gasket in FIG. 6 along the axes A-A and B-B, respectively;

DESCRIPTION OF THE EMBODIMENTS

In the following description, reference is made to the accompanying drawings that form a part thereof, and in which are shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, not to be taken in a limited sense.

As used herein, the term "microtiter plate" is also known as a "sample plate," "microtitration plate," and "microplate" interchangeably and refers to a multi-welled sample receptacle for testing of chemical and biological samples. Microplates can have wells that are conical, cylindrical, rectilinear, tapered, and/or flat-bottomed in shape, and can be constructed of a single material or multiple materials. A standard microtiter plate conforms to SBS Standards. Microtiter plates can be open-faced (e.g. closed with a sealing film or caps) or close-chambered (e.g. microcard as described in U.S. Pat. No. 6,825,047). Open-faced microtiter plates can be filled, for example, with pipettes (hand-held, robotic, etc.) or through-hole distribution plates. Close-chambered microtiter plates can be filled, for example, through channels or by closing to form the chamber. Examples of standard microtiter plates have the following number of wells or chambers: 24, 48, 96, 384, or 1536.

FIGS. 1 to 14 depict exemplary embodiments of methods and systems that include a plurality of reaction vessel receiving elements thermally decoupled and each segment assigned a thermoelectric cooler (TEC), also Peltier cooler, which may be actuated independently.

By this means the individual reaction vessel receiving element of the device may be set to different temperatures independently of one another. This makes it possible not only to set different temperature levels in the segments, but also for them to be held for varying lengths of time or altered at different rates of change. The device according to the invention thus permits optimization of all physical parameters critical for a PCR process, while the optimization process may be carried out on a single reaction vessel receiving element in which a single standard microtiter plate may be inserted.

With the device according to the invention it is therefore also possible to optimize the residence times and rates of temperature change without having to distribute the reaction mixture over different microtiter plates for this purpose. Moreover, it is also possible to optimize the mixture volume by varying the mixture volume over different reaction vessel segments. The thermal cycling device according to the invention is in particular suitable for optimizing the multiplex PCR process, in which several different primers are used.

Figure 1:
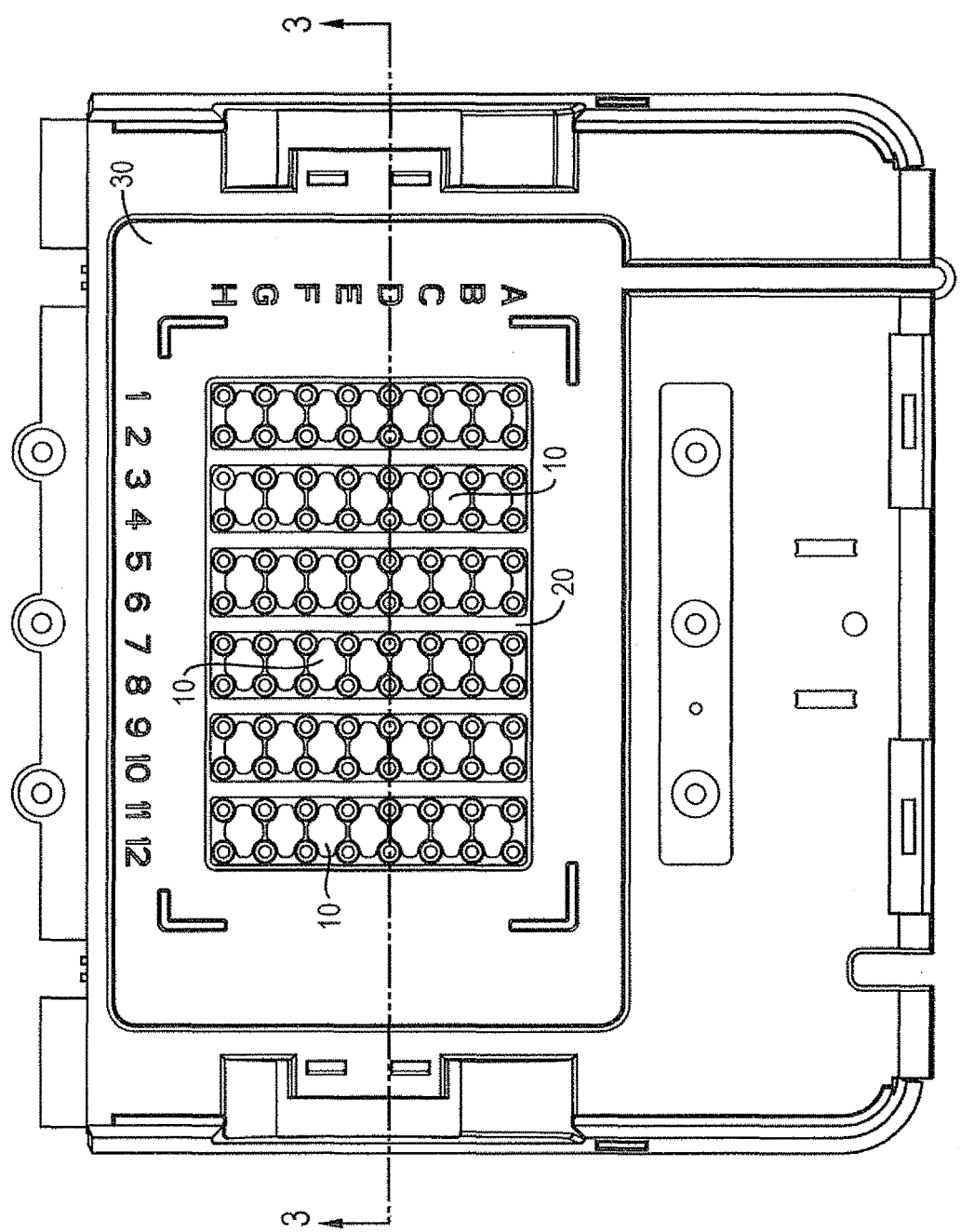
FIG. 1 depicts a top view of a portion of a device according to the invention for carrying out chemical or biological reactions in accordance with an exemplary embodiment showing the reaction vessel receiving elements, gasket, and drip pan.

According to various embodiments, FIG. 1 shows a top view of a portion of a device according to the invention for carrying out chemical or biological reactions in accordance with an exemplary embodiment showing the reaction vessel receiving elements 10, gasket 20, and drip pan 30.

Figure 2:
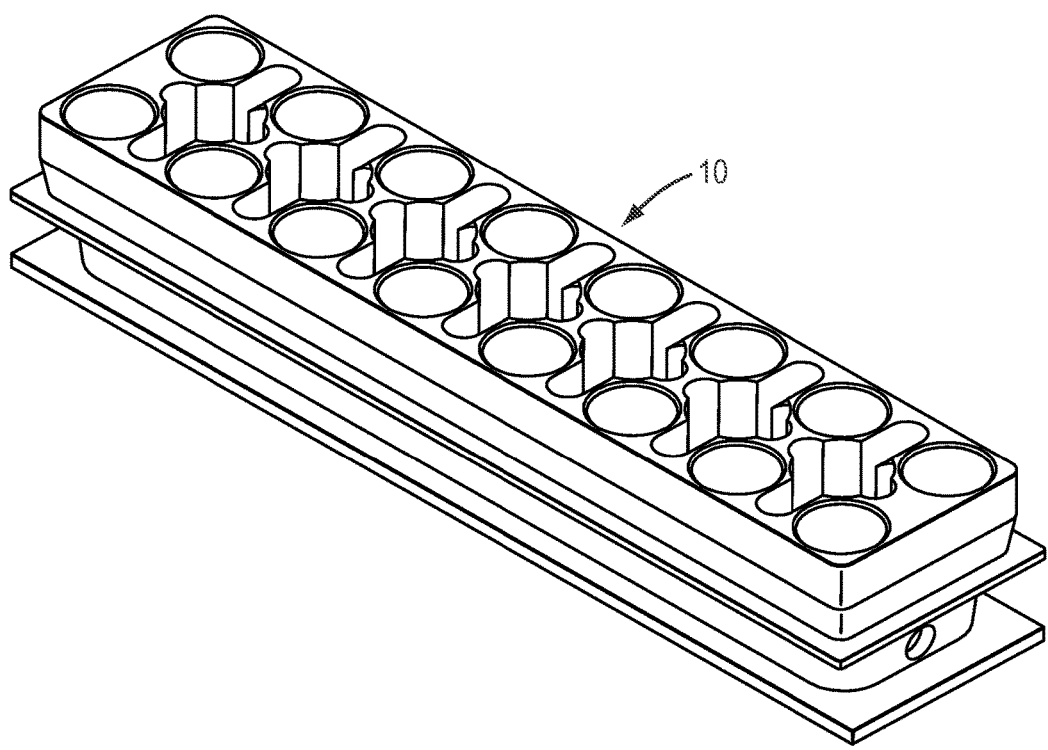
FIG. 2 depicts a perspective view of a reaction vessel receiving element, according to various embodiments.
Figure 3:
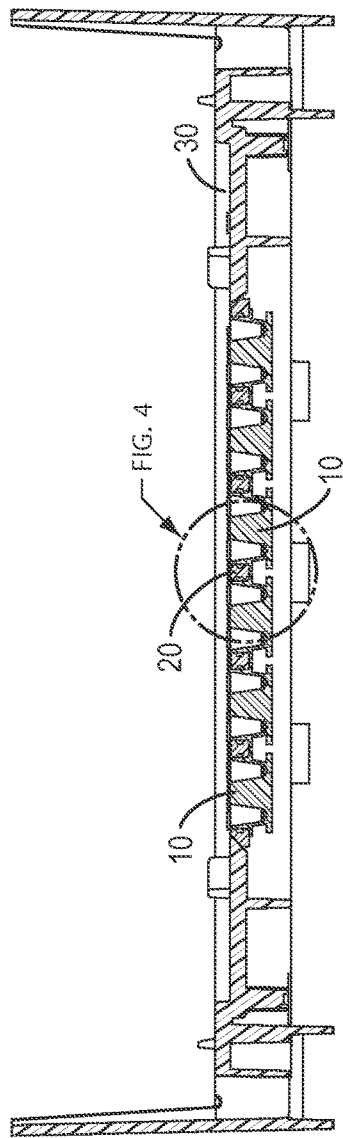
FIG. 3 depicts a cross-sectional view of the device of along the axis shown in FIG. 1.
Figure 4:
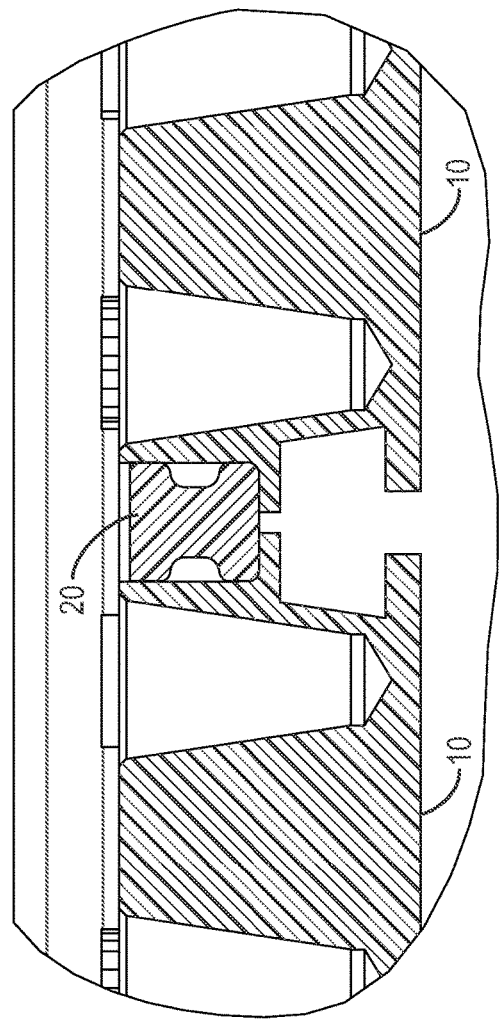
FIG. 4 depicts a magnified view of a portion of FIG. 3.
Figure 5:
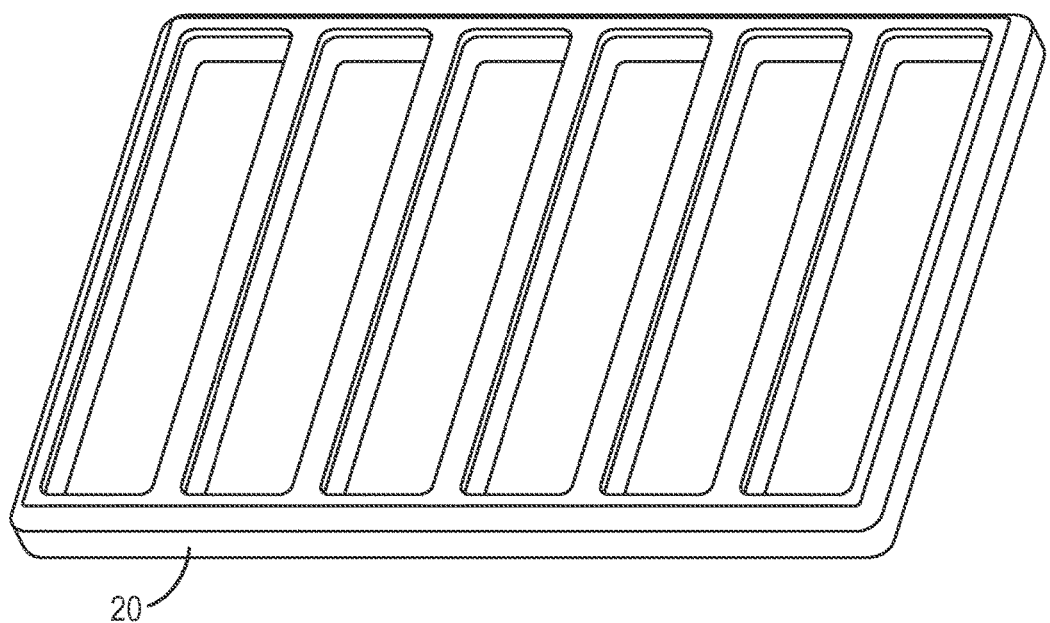
Figure 9:
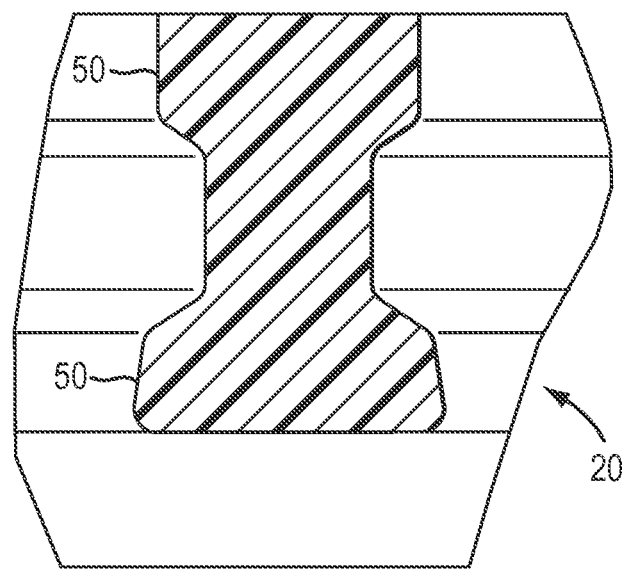
FIGS. 9 and 10 depict magnified views of portions of FIG. 7.
Figure 10:
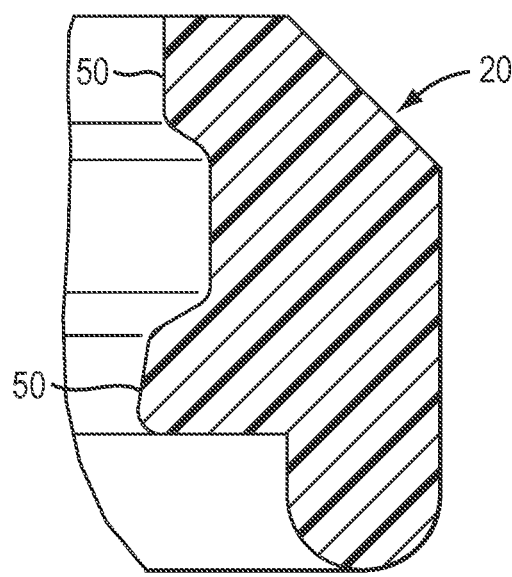
Figure 11A:
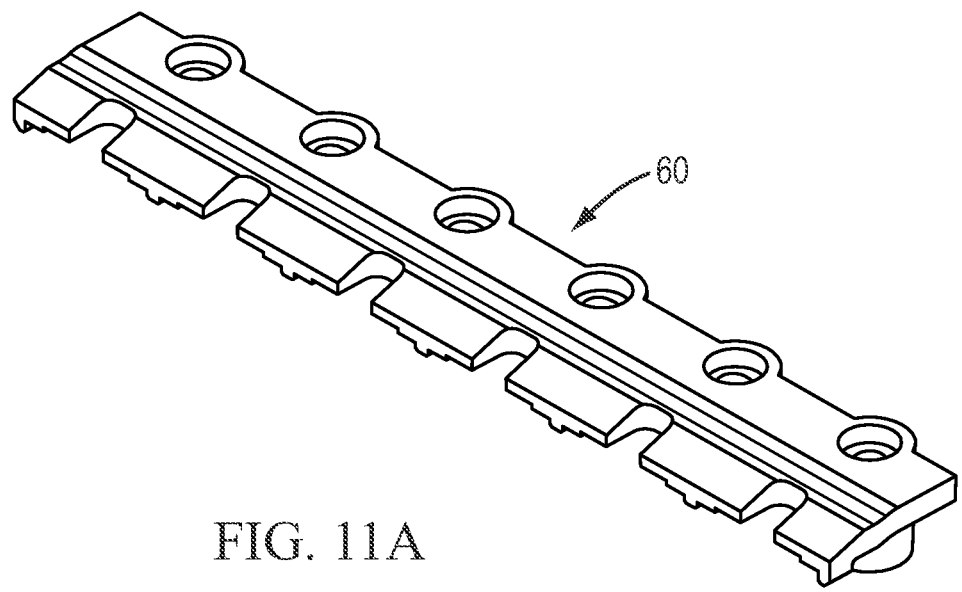
FIGS. 11A and 11B depict top and bottom perspective views of the clamp, according to various embodiments.
Figure 11B:
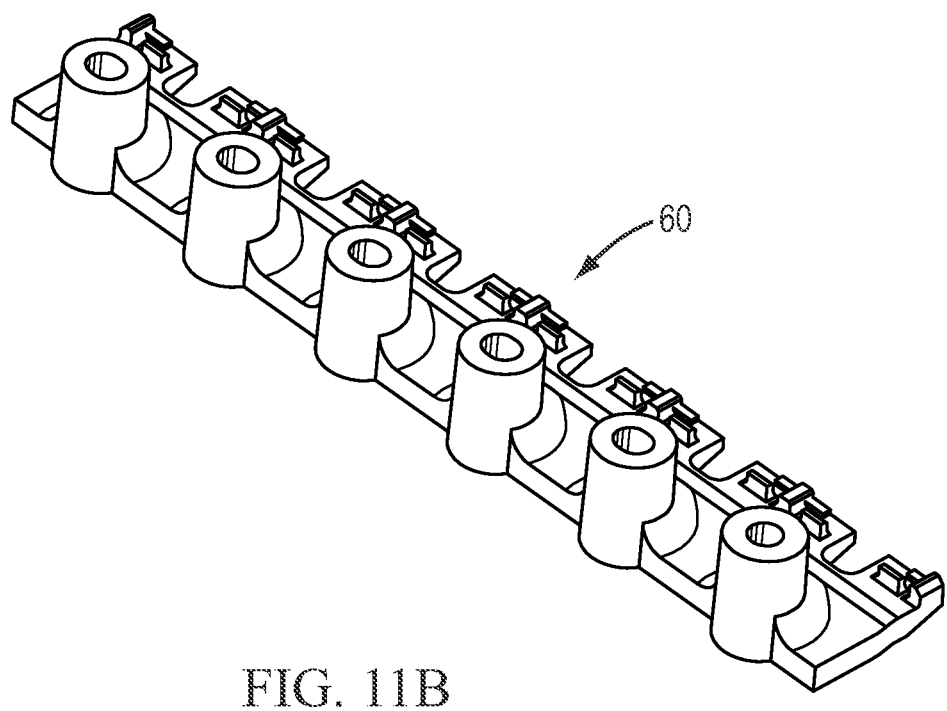

According to various embodiments, FIGS. 2-4 shows the recesses of a reaction vessel receiving element 10 and how a plurality reaction vessel receiving elements 10 are configures to be surrounded by gasket 20 and drip pan 30 to form an airtight seal between each of the plurality of reaction vessel receiving elements and between the drip pan and the plurality of reaction vessel receiving elements 10 to isolate the plurality of TECs 40 below each reaction vessel receiving element 10 from environmental conditions above the drip pan 30 and the plurality of reaction vessel receiving elements 10. This is achieved by sealing the area below the plurality of reaction vessel receiving elements 10 with a gasket 20 that has a convex construction as shown in FIGS. 4-10. The gasket 20 has a convex portion with ribs 50 that provide contact the plurality of reaction vessel receiving elements 10. The clamp 60 as shown in FIGS. 11A and 11B provides a lateral force to compress the gasket between the reaction vessel receiving elements 10 to form an airtight seal between each of the plurality of reaction vessel receiving elements 10.

Figure 12:
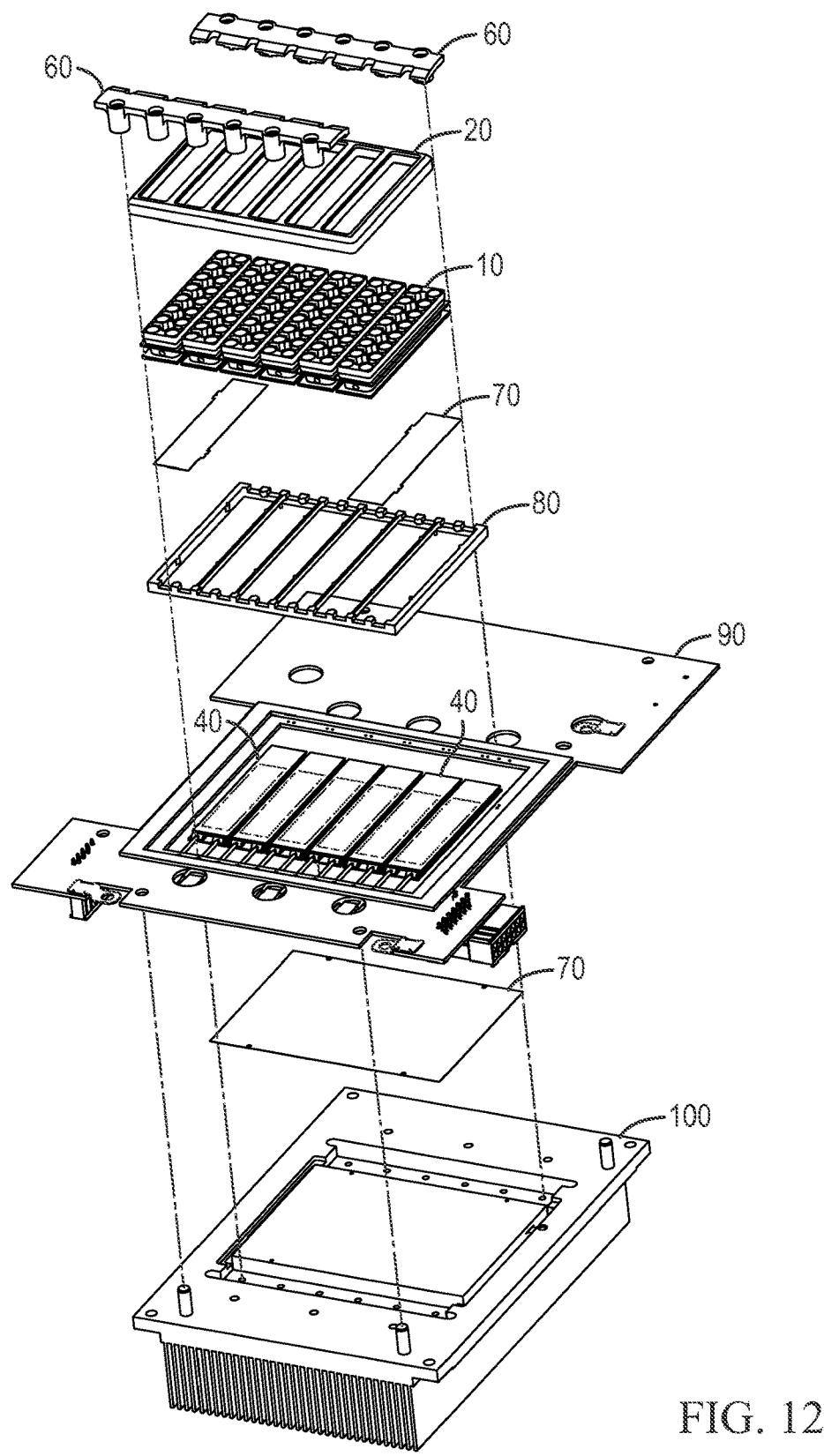
FIG. 12 depicts an exploded view of the bottom portion of a thermal cycler, according to various embodiments.

According to various embodiments, FIG. 12 shows an exploded view of the bottom portion of a thermal cycler with the clamp 60 providing lateral force to the plurality of reaction vessel receiving elements 10 to compress gasket 20. Each reaction vessel receiving element 10 is coupled to a TEC 40 via a thermally conductive material 70. The TECs 40 are aligned by frame 80 and powered by a printed circuit board 90. The TECs 40 are coupled to heat sink 100 by thermally conductive material 70. The clamp 60, in addition to providing lateral force to the plurality of reaction vessel receiving elements 10, can provide vertical clamping of the plurality of reaction vessel receiving elements 10 to the TECs 40 and heat sink 100. The TECs can be powered by current flow from a plurality of power amplifiers. The power amplifiers can be coupled to the TEC via actual leads or can be coupled via infrared connection to permit tighter placement of TECs and reaction vessel receiving elements 10. According to various embodiments, the present teachings contemplate one or more temperature sensors disposed in each reaction vessel receiving element in conjunction with each TEC. According to various embodiments, the present teachings contemplate a heating element disposed in each reaction vessel receiving element, wherein the heating element provides fine heating to a control temperature. According to various embodiments, the present teachings contemplate a plurality of power amplifiers, and a switch for each of the plurality of reaction vessel receiving elements to direct a current flow from the plurality of power amplifiers to the TEC. According to various embodiments, the present teachings contemplate the TECs corresponding to each of the reaction vessel receiving elements are integrated into a single unit. In various embodiments, the TEC can include dicing to segment portions according to the reaction vessel receiving elements.

According to various embodiments, the present teachings contemplate a reaction vessel receiving elements comprises a flat surface sample block.

Figure 13:
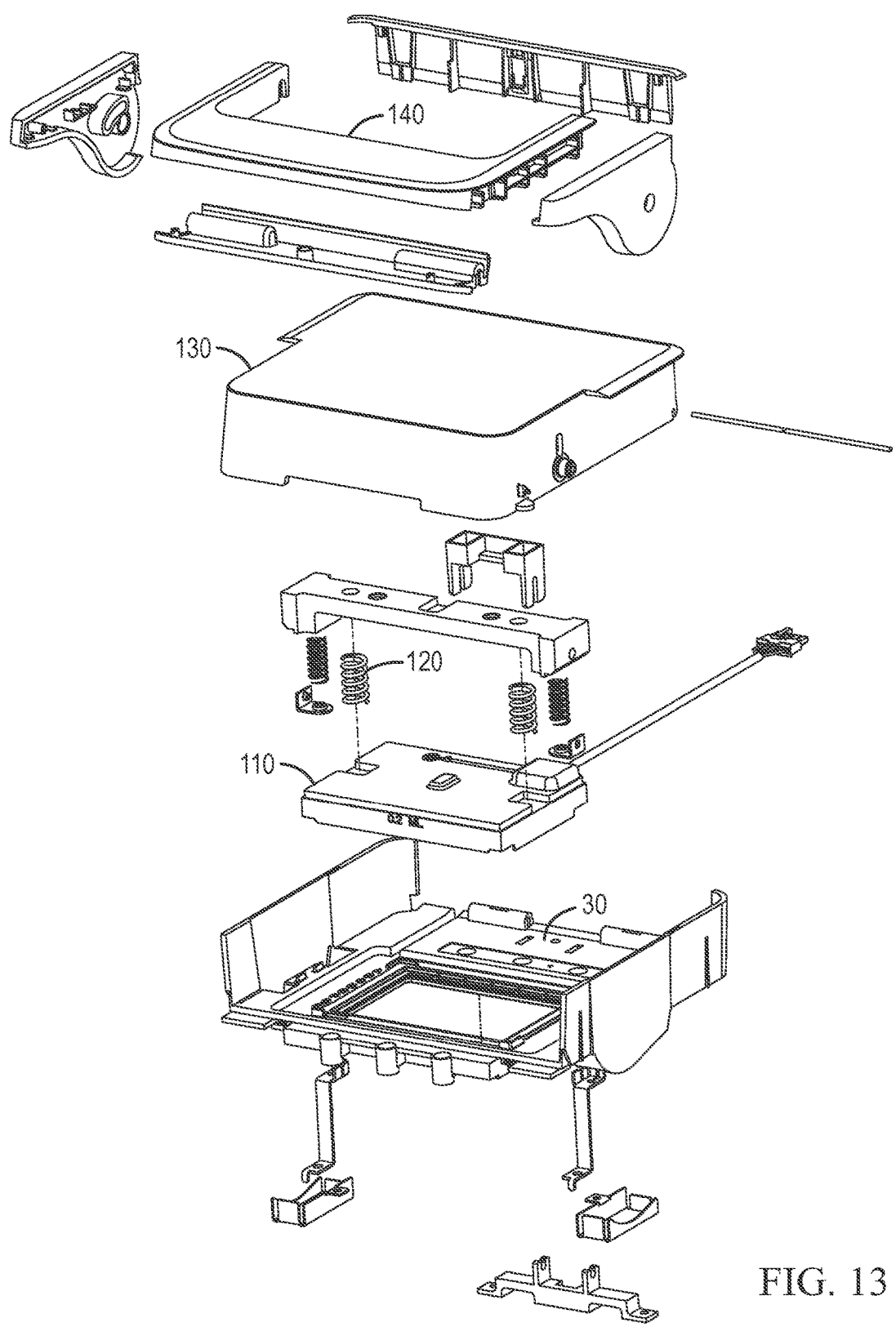
FIG. 13 depicts an exploded view of the top portion of a thermal cycler, according to various embodiments.

According to various embodiments, FIG. 13 shows an exploded view of the top portion of a thermal cycler with drip pan 30 and the heated lid, including heated platen 110, springs 120 to provide a downward force to press the heated platen 110 on the microtiter plate, cover 130 to enclose the heated platen 110 and springs 120, and locking handle mechanism 140 to close, lower, and lock the heated lid in place over the microtiter plate sitting in the plurality of reaction vessel receiving elements 10.

Figure 14:
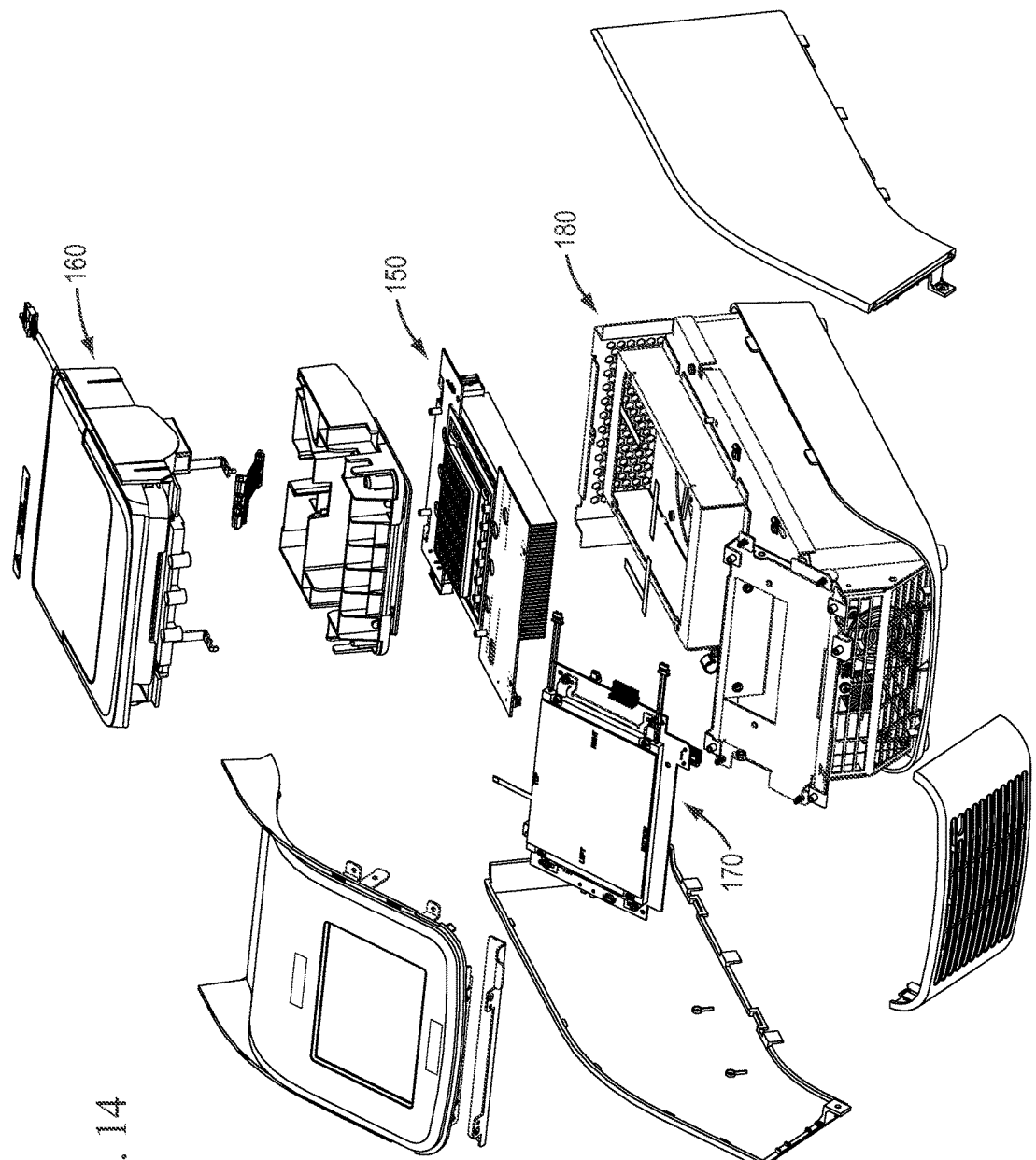
FIG. 14 depicts an exploded view of a thermal cycler, according to various embodiments.

According to various embodiments, FIG. 14 shows a thermal cycler instrument with the exploded view of FIG. 12 as bottom portion 150, and the exploded view of FIG. 13 as top portion 160 with additional display/touch screen 170 and electrical housing 180.

The reaction vessel receiving elements 10 are not influenced by the other reaction vessel receiving elements 10, and their temperature may be set completely independently of the other reaction vessel receiving elements 10. By this means it is possible to run quite different temperature cycles on the individual reaction vessel receiving elements 10, with one of the reaction vessel receiving element 10 for example heated up to the denaturing temperature and another held at the annealing temperature. Thus it is possible for the residence times, i.e. the intervals of time for which the denaturing temperature, the annealing temperature and the elongation temperature are held, also the rates of temperature change, to be set as desired, and run simultaneously on the individual reaction vessel receiving elements 10. In this way it is possible to optimize not only the temperatures, but also the residence times, mixture volume, and the rates of temperature change. According to various embodiments, the present teachings provide for a method of annealing samples in a first portion of the microtiter plate at a first annealing temperature by cooling a first reaction vessel receiving element, and annealing samples in a second portion of the microtiter plate at a second annealing temperature by cooling a second reaction vessel receiving element, wherein the second annealing temperature is not equal to the first annealing temperature. According to various embodiments, the present teachings provide for a method of elongating samples in a first portion of the microtiter plate at a first elongation temperature by heating a first reaction vessel receiving element, and elongating samples in a second portion of the microtiter plate at a second elongation temperature by heating a second reaction vessel receiving element, wherein the second elongation temperature is not equal to the first elongation temperature. According to various embodiments, the present teachings provide for a method of repeating for a first number of cycles at least one of the steps of denaturing, annealing, and elongating samples in a first portion of the microtiter plate corresponding to a first reaction vessel receiving element, and repeating for a second number of cycles at least one of the steps of denaturing, annealing, and elongating samples in a second portion of the microtiter plate corresponding to a second reaction vessel receiving element, wherein the first number of cycles is not equal to the second number of cycles. According to various embodiments, the present teachings provide for a method where a rate of cooling of a first reaction vessel receiving element is not equal to the rate of cooling of a second reaction vessel receiving element, and/or a rate of heating of a first reaction vessel receiving element is not equal to the rate of heating of a second reaction vessel receiving element. According to various embodiments, the present teachings provide for a method where the samples in a first reaction vessel receiving element have a different volume than the samples in a second reaction vessel receiving element. According to various embodiments, the present teachings provide for a method where a first reaction vessel receiving element is kept at a first residence time for annealing samples and a second reaction vessel receiving element is kept at a second residence time for annealing samples. According to various embodiments, the present teachings provide for a method where a first reaction vessel receiving element is kept at a first residence time for elongating samples and a second reaction vessel receiving element is kept at a second residence time for elongating samples According to various embodiments, infrared sensors may for example be used as temperature sensors, located e.g. in the cover. With this sensor arrangement it is possible to sense the temperature of the reaction mixture directly. According to various embodiments, the heated platen 110 can be sub-divided into segments that correspond to the reaction vessel receiving elements 10 so that each reaction vessel receiving element 10 can have an independently controlled heated platen segment that can be varied in temperature. This variance can achieve optimized heated lid conditions and/or provide heated platen segments to track the cycling of the reaction vessel receiving elements 10.

According to various embodiments, the reaction vessel receiving elements 10 are made from a metal with good heat conducting properties, e.g. aluminum, copper, nickel, and/or silver. According to various embodiments, reaction vessel receiving elements 10 can be machined, electroformed, or formed by metal injection molding (MIM). MIM can combine the design freedom of plastic injection molding with the performance of metal. MIM can be used with metals such as aluminum, copper, tungsten, and alloys thereof.

According to various embodiments, the gasket 20 is made from non-heat conducting materials or thermally insulating materials are either plastics or ceramics, for example silicone. The gasket 20 can also be flexible to provide an airtight seal. An example of hardness to provide such flexibility is durometer 30 shore A. According to various embodiments, drip pan 30 can be formed of any suitable material including but not limited to a thermoplastic. One of ordinary skill in the art understands that the disclosed drip pans are exemplary and that the drip pan can be configured to receive the outer skirts of standard microtiter plates.

According to various embodiments the drip pan 30 has demarcations for the standard microtiter plate, for example twelve columns (shown as columns 1-12) and 8 rows (shown as rows A-H) of wells. Although a 96 well sample plate with 16 wells in each reaction vessel receiving element 10 is shown, one of ordinary skill in the art will understand that more or less wells can be included in each reaction vessel receiving element. One of ordinary skill in the art will also understand that six reaction vessel receiving elements 10 is exemplary and that more or less than six reaction vessel receiving elements 10 is contemplated.

The invention is described above with the aid of embodiments with 96 recesses for receiving a microtiter plate with 96 reaction vessels. The invention is not, however, limited to this number of recesses. Thus for example the reaction vessel receiving element may also have 384 recesses to receive a corresponding microtiter plate. With regard to features of the invention not explained in detail above, express reference is made to the claims and the drawing.

According to various embodiments, solid heated platen 110, can be replaced with an apertured heated lid or a transparent heated lid to permit detection of samples in the standard microtiter plate during amplification, e.g. real-time PCR. According to various embodiments, an excitation light source and a detector can be included in cover 130 to provide the mechanism for detection of sample held in the standard microtiter plate. In various embodiments, the reaction vessel receiving element 10 can be combined with an excitation light source and a detector to provide monitoring of real-time PCR in samples in each of the reaction vessel receiving elements 10. Real-time PCR can be monitored by detecting luminescence (for example, fluorescence, chemiluminescence, etc.) during the thermal cycling. In various embodiments, the monitoring can be provided by imaging optics to optically couple the samples in each of the reaction vessel receiving elements 10 with a detector, such as a CCD or PMT. Examples of fluorescence detection with imaging optics embodiment are shown for example at U.S. Pat. Nos. 7,295,316 and 7,423,750, both herein incorporated by reference in their entirety. According to various embodiments, a reaction vessel receiving element 10 is associated with different regions on the detector, for example, a CCD. The detector can be calibrated such that the regions corresponding to the assays that are performed in each reaction vessel receiving element 10 so that detection of the fluorescence is more efficient. According to various embodiments, the excitation light source can be one or more LEDs used to provide improved illumination wavelength uniformity, light power output uniformity, and minimal degradation of output over extended periods of time. Further, LEDs operate at relatively low temperatures and require little or no external cooling. According to various embodiments, the detection optics can have sets of excitation filters, dichroic mirrors (beam-splitters), and emission filters. Alternatively, filter wheels on the emission side and/or excitation side can provide different excitation and emission light patterns. According to various embodiments, the present teachings describe a thermal cycler with an excitation light source and a detector for monitoring real-time PCR that can include imaging optics optically coupling the samples in the plurality of reaction vessel receiving elements with a CCD or a scanning head optically coupling the samples in the plurality of reaction vessel receiving elements by movement over those segments.

The term "excitation light source" as used herein refers to a source of irradiance that can provide excitation that results in fluorescent emission. Light sources can include, but are not limited to, LEDs, phosphor coated LEDs, organic LEDs (OLED), phosphorescent OLEDs (PHOLED), inorganic-organic LEDs, LEDs using quantum dot technology, and LED arrays. Alternatively, the light sources can include white light, halogen lamp, lasers, solid state laser, laser diode, micro-wire laser, diode solid state lasers (DSSL), vertical-cavity surface-emitting lasers (VCSEL), thin-film electroluminescent devices (TFELD), filament lamps, arc lamps, gas lamps, and fluorescent tubes. Light sources can have high radiance, such as lasers, or low radiance, such as LEDs. Radiance refers to light emitted and can be measured in units of watts per centimeter squared per steradian. Lasers have high radiance since they emit light in substantially a single direction. LEDs have low radiance since they typically emit light into 2 pi steradians. The different types of LEDs mentioned above can have a medium to high radiance.

The term "detector" as used herein refers to any component, portion thereof, or system of components that can detect light including a charged coupled device (CCD), back-side thin-cooled CCD, front-side illuminated CCD, a CCD array, a photodiode, a photodiode array, a photomultiplier tube (PMT), a PMT array, complimentary metal-oxide semiconductor (CMOS) sensors, CMOS arrays, a charge-injection device (CID), CID arrays, etc. The detector can be adapted to relay information to a data collection device for storage, correlation, and/or manipulation of data, for example, a computer, or other signal processing system.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A thermal cycler for processing biological or chemical samples comprising:
    a plurality of independent reaction vessel receiving elements configured to receive one standard microtiter plate;
    a plurality of thermoelectric cooling devices disposed to correspond to the plurality of reaction vessel receiving elements, the thermoelectric cooling devices configured to provide heating and cooling;
    a drip pan positioned above the thermoelectric cooling devices and framing the reaction vessel receiving elements;
    a single flexible gasket positioned between the drip pan and the reaction vessel receiving elements isolating the plurality of reaction vessel receiving elements from each other, and isolating the thermoelectric cooling devices from environmental conditions above the drip pan; and
    a clamp comprising a first portion and a second portion orthogonal to the first portion, the first portion positioned around the exterior of the gasket thereby providing a lateral force that compresses the gasket between the reaction vessel receiving elements, and the second portion positioned above the plurality of reaction vessel receiving elements thereby providing a vertical force that compresses the plurality of reaction vessel receiving elements against the thermoelectric cooling devices,
    wherein the gasket is composed of non-thermally conducting material that provides thermal isolation between adjacent reaction vessel receiving elements and comprises a plurality of ribs that provide contact to the plurality of reaction vessel receiving elements and the drip pan, whereby the gasket and the drip pan form an airtight seal between each of the plurality of reaction vessel receiving elements and between the drip pan and the plurality of reaction vessel receiving elements.

2. The thermal cycler of claim 1, further comprising one or more temperature sensors disposed in each reaction vessel receiving element.

3. The thermal cycler of claim 1, further comprising a heating element disposed in each reaction vessel receiving element, wherein the heating element provides fine heating to a control temperature.

4. The thermal cycler of claim 1, further comprising:
a plurality of power amplifiers; and
a switch for each of the plurality of reaction vessel receiving elements to direct a current flow from the plurality of power amplifiers to the thermoelectric cooling devices.

5. The thermal cycler of claim 1, wherein each reaction vessel receiving element comprises a flat surface sample block.

6. The thermal cycler of claim 1, wherein each thermoelectric cooling device corresponding to each reaction vessel receiving element is integrated into a single unit.

7. The thermal cycler of claim 6, wherein thermoelectric cooling device comprise dicing.

8. The thermal cycler of claim 1, wherein the reaction vessel receiving elements are formed by one of metal injection molding (MIM), machining, and electroforming.

9. The thermal cycler of claim 1, further comprising an excitation light source and a detector for monitoring real-time PCR.

10. The thermal cycler of claim 9, further comprising imaging optics optically coupling the samples in the plurality of segments with a CCD.

11. The thermal cycler of claim 9, further comprising a scanning head optically coupling the samples in the plurality of segments by movement over those segments.

12. The thermal cycler of claim 1, wherein the clamp is configured to couple to a top portion of the reaction vessel receiving elements.

13. The thermal cycler of claim 1, further comprising a heated lid.

14. The thermal cycler of claim 13, wherein the heated lid comprises a heated platen and a set of springs, the springs configured to provide downward force to press the platen against the microtiter plate.

15. The thermal cycler of claim 14, wherein the heated lid further comprises a cover shaped to enclose the heated platen and springs.

16. The thermal cycler of claim 15, wherein the cover comprises of an excitation light source and an associated detector.

17. The thermal cycler of claim 1, wherein the thermoelectric cooling devices are coupled to a heat sink.

18. The thermal cycler of claim 1, wherein the thermoelectric cooling devices are coupled to a plurality of power amplifiers, each power amplifier being coupled to each thermoelectric cooling device by an infrared connection.

* * * * *